United States Patent [19]

Davenport

[11] Patent Number: 4,743,254
[45] Date of Patent: May 10, 1988

[54] SMALL INCISION INTRAOCULAR LENS

[75] Inventor: James M. Davenport, Laguna Niguel, Calif.

[73] Assignee: American Hospital Supply Company, Deerfield, Ill.

[21] Appl. No.: 697,215

[22] Filed: Jan. 31, 1985

[51] Int. Cl.⁴ .............................................. A61F 2/16
[52] U.S. Cl. ...................................................... 623/6
[58] Field of Search ..................... 623/6; 351/162–165

[56] References Cited

U.S. PATENT DOCUMENTS

| | | | |
|---|---|---|---|
| 2,043,840 | 6/1936 | Singer | 351/165 |
| 3,034,403 | 5/1962 | Neefe | 623/6 X |
| 3,454,332 | 7/1969 | Siegel | 351/162 |
| 4,435,856 | 3/1984 | L'Esperance | 623/6 |
| 4,451,938 | 6/1984 | Kelman | 623/6 |
| 4,601,722 | 7/1986 | Kelman | 623/6 |
| 4,605,409 | 8/1986 | Kelman | 623/6 |
| 4,664,665 | 5/1987 | Reuss et al. | 623/6 |

FOREIGN PATENT DOCUMENTS

| | | | |
|---|---|---|---|
| 0099641 | 1/1984 | European Pat. Off. | 623/6 |
| 2114315 | 8/1983 | United Kingdom | 623/6 |

OTHER PUBLICATIONS

The Rayner Choyce Mark VIII, Anterior Chamber Implant, Catalogue No. 469, Rayner & Keeler Limited, 3 pages.
"Glare Disability in Eyes With Intraocular Lenses", American Journal of Ophthalmology, Daniel J. Nadler, M.D., et al., vol. 97, Jan. 1984, pp. 43–47.

Primary Examiner—Ronald L. Frinks
Attorney, Agent, or Firm—Gordon L. Peterson

[57] ABSTRACT

An intraocular lens comprising an elongated optic and first and second glare-reducing sections extending along the elongated sides of the optic. The glare-reducing sections are joined to each other and to the optic by a joining section. The joining section is flexible so that the glare-reducing sections can be moved over the optic to reduce the overall dimensions of the intraocular lens for implantation. Fixation members fix the intraocular lens in the eye.

12 Claims, 4 Drawing Sheets

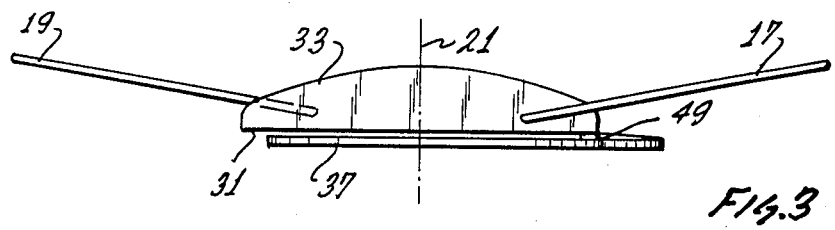
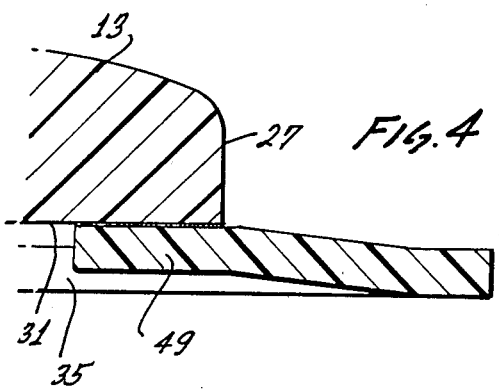
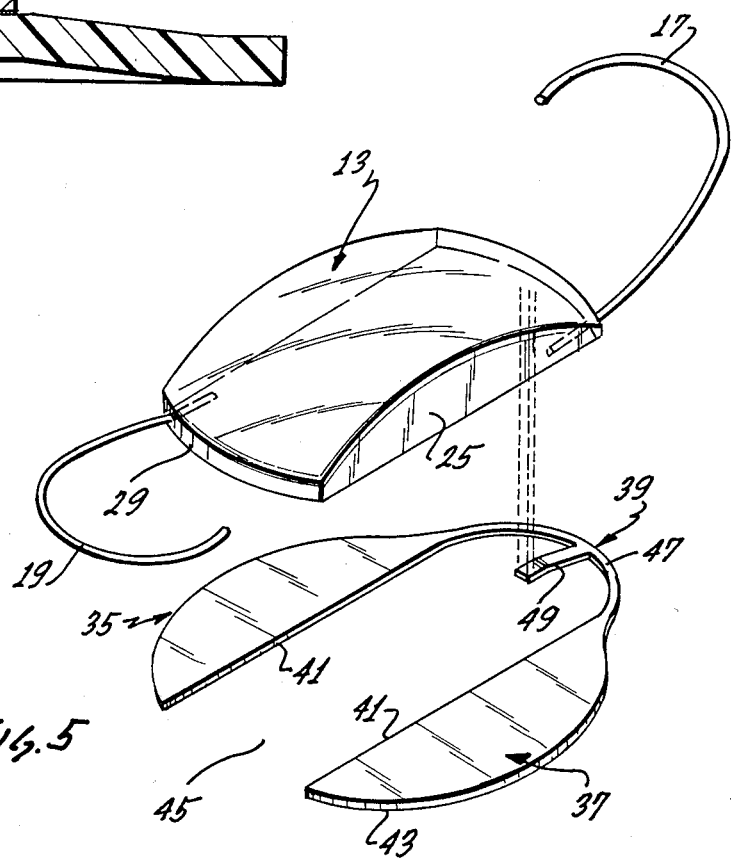

SMALL INCISION INTRAOCULAR LENS

BACKGROUND OF THE INVENTION

Cataract surgery generally involves the removal of the natural lens and the implantation of an intraocular lens. Both extracapsular lens removal, which leaves the posterior capsule, and intracapsular removal in which the natural lens is removed, together with the lens capsule, require relatively large incisions in the eye of the order of 7 to 8 millimeters in length. Phacoemulsification, which breaks up the natural lens with ultrasound and removes the pieces, requires a small incision of only about 3 to 3½ millimeters in length.

A small incision in the eye is greatly preferred because it produces less trauma, minimizes fluid losses, reduces the likelihood of infection and inflammation and minimizes and facilitates the suturing required to close the incision. Although phacoemulsification requires only a small incision for removal of the natural lens, the optic of the intraocular lens is typically of the order of 6 millimeters in diameter and, therefore, is too large to pass through the 3 to 3½ millimeter incision. Accordingly, even if phacoemulsification is used, it is necessary to enlarge the incision in order to insert the intraocular lens.

In an effort to overcome this, it has been proposed in Kelman U.S. Pat. No. 4,451,938 to construct the intraocular lens in multiple pieces, insert the pieces separately into the eye and then assemble them within the eye. Unfortunately, the surgical techniques required for assembly of the individual pieces of intraocular lens in the eye are extremely difficult.

It has also been proposed in Mazzocco British Patent Application No. 2,144,315 and Kelman European Patent Application No. 83303414.3 to utilize a deformable optic which can be folded for insertion through a small incision into the eye. One problem with this approach is that it has been difficult to find materials which are both adequately deformable and suitable for use as an optic.

SUMMARY OF THE INVENTION

This invention generally overcomes the disadvantages noted above by providing an optic which has at least one dimension which is small enough to pass through a relatively short or small incision, such as a 3 to 3.5 millimeter incision. Unlike the prior art discussed above, the optic can be rigid and be integrally constructed in a single piece so that no folding or assembly of the optic is necessary.

The optic can be provided with a suitably small dimension or dimensions in various different ways. For example, the optic may be circular and have a reduced diameter. However, to increase the area of the optic in a direction transverse to the optical axis of the lens while providing a small dimension to enable insertion through a small incision, the optic is preferably elongated. Preferably, the optic is in the form of a central segment of a circle.

The eye has an active optical region which is approximately 5 to 6 millimeters in diameter and which is transverse to the optical axis of the eye. Light passing through this region of the eye can be focused by the lens on the retina and, therefore, seen. However, because a dimension of the optic is less than 5 to 6 millimeters, light within the active optical region which does not pass through the optic would produce glare.

This invention provides glare-reducing means to reduce or eliminate the glare resulting from light in the active optical region which does not pass through the optic. Generally, the glare-reducing means can be any means or member capable of reducing the glare observed by the patient who wears the intraocular lens. For example, the glare-reducing means may reduce the transmission of light through the active optical region to the retina. For example, the glare-reducing means may transmit no more than about 60 percent of the visible light incident thereon, although preferably it transmits no more than about 10 percent of such light. For optimum glare-reducing results, the glare-reducing means is essentially opaque so that it transmits no more than about 1 percent of such light. However, to achieve this low a percent of transmission, the glare-reducing means would need to be black, and this is undesirable. Accordingly, the overall preferred construction is one which achieves the lowest percent of visible light transmission without making the glare-reducing means black, and this may be about 10 percent transmission.

The glare-reducing means reduces glare resulting from light in that portion of the active optical region which does not pass through the optic. Because the active optical region is generally circular, the glare-reducing means is preferably present in any region of this circle not occupied by the optic. To the extent that the glare-reducing means is not operative in this region, the glare will increase. Accordingly, for optimum results, the glare-reducing means should be effective throughout the active optical region where the optic is not present.

The provision of glare-reducing means, however, increases the dimensions of the intraocular lens so that it will not pass through the relatively short 3 to 3.5 millimeter incision. To solve this problem, this invention provides that at least a portion of the glare-reducing means be deformable to permit a reduction in an overall dimension of the intraocular lens to facilitate implantation.

The glare-reducing means is not part of the optic in that it does not focus light on the retina. In addition, the glare-reducing means transmits a lower percentage of incident visible light than the optic and has a different power than the optic.

The glare-reducing means preferably includes a first glare-reducing section extending along one of the elongated sides of the optic and a joining section which joins the first glare-reducing section to the optic. In a preferred construction, the glare-reducing means includes a second glare-reducing section which extends along the other elongated side of the optic and is coupled to the joining section.

The optic has opposite ends, and the joining section advantageously projects beyond one of the ends to form a lead-in to facilitate implantation. The optic has a posterior face, and the glare-reducing sections overlap the posterior face of the optic along the associated elongated sides to assure that light transmission is reduced or eliminated outside the optic.

The glare-reducing sections are preferably, flexibly joined to the joining section so they can be moved over the optic for implantation. Because the glare-reducing sections are preferably located posteriorly of the posterior face of the optic, they can be moved over the posterior face without interference from the optic. The glare-reducing sections may be rigid.

BRIEF DESCRIPTION OF THE DRAWINGS

FIG. 3 is a side elevational view of the intraocular lens.

FIG. 4 is an enlarged, fragmentary sectional view taken generally along line 4—4 of FIG. 1.

FIG. 5 is an exploded isometric view of the intraocular lens.

DESCRIPTION OF THE PREFERRED EMBODIMENT

Figure 1:
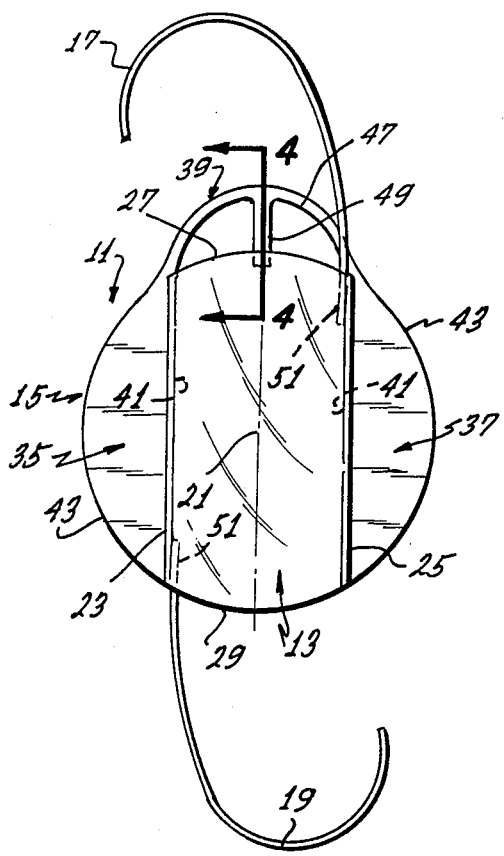
FIG. 1 is a front elevational view of an intraocular lens constructed in accordance with the teachings of this invention.

FIGS. 1–5 show an intraocular lens 11 which comprises a rigid optic 13, glare-reducing means in the form of a glare attachment 15 and fixation means in the form of resilient loops 17 and 19 for affixing the intraocular lens within the eye. Although the optic 13 can be of various sizes and configurations, in the embodiment illustrated, it has an optical axis 21, and it is elongated in a direction generally transverse to the optical axis such that the optic has elongated, planar, parallel sides 23 and 25 and opposite ends 27 and 29. In the embodiment illustrated, the optic 13 is in the form of a central segment of circle, and thus the ends 27 are circular. The optic 13 has a posterior face 31 and an anterior face 33, and in the embodiment illustrated, the posterior face is planar, and the anterior face is convex.

The glare attachment 15 reduces glare resulting from light in a zone which extends along the elongated sides 23 and 25 of the optic 13 when the intraocular lens 11 is implanted as described more fully hereinbelow in connection with FIGS. 9 and 10. The glare attachment 15 may be formed by machining and, like the optic 13, may be integrally constructed of polymethylmethacrylate or other suitable material for implantation in the eye.

Generally, the glare attachment in this embodiment comprises glare-reducing sections 35 and 37 and a joining section 39 which joins the glare-reducing sections to each other and to the optic 13. The glare-reducing sections 35 and 37 may be identical, and each of them has a linear, inner edge 41 and a curved part-circular outer edge 43. Each of the glare-reducing sections 35 and 37 forms an outer segment of a circle and is in the form of a thin disc having flat, opposed, parallel faces. As shown in FIG. 5, the inner edges 41 are widely spaced by a slot 45 which extends all the way to the joining section 39. Each of the glare-reducing sections 35 and 37 transmits a substantially lower percent of visible incident light than the optic 13, and in this embodiment, each of them transmits no more than about 10 percent of such incident visible light.

The joining section 39 includes a thin web 47 in the form of a shallow "U" which integrally joins adjacent ends of the glare-reducing sections 35 and 37. The joining section 39 also includes an elongated finger or tab 49 which projects into the slot 45 as shown in FIG. 5 and which projects upwardly out of the plane of the glare-reducing sections 35 and 37 as shown in FIG. 4. The web 47 is resiliently deformable so that the glare-reducing sections can be moved relative to each other. In the unrestrained condition, the web 47 retains the glare-reducing sections 35 and 37 in the position shown in FIGS. 1–5 in which the edges 41 are parallel, and the glare-reducing sections 35 and 37 are co-planar.

Although the glare attachment 15 could be directly or indirectly coupled to the optic 13 in various different ways, in the embodiment illustrated, it is directly coupled to the optic by sonic welding an end portion of the tab 49 to the posterior face 31 adjacent the end 27 as shown in FIGS. 1 and 4. With the glare attachment 15 coupled to the optic 13 in this manner, the optic 13 lies just anteriorly of, and centered on, the slot 45, and the glare-reducing sections 35 and 37 extend along the sides 23 and 25, respectively, of the optic 13.

To facilitate appropriate, inward movement of the glare-reducing sections 35 and 37, they are preferably located in a plane which lies just posterior of the posterior face 31 as best shown in FIG. 3. To assure that there is no gap between the optic 13 and the glare-reducing sections 35 and 37, inner edge portions of the glare-reducing sections along the inner edges 41 overlap outer edge portions of the optic 13 along the sides 23 and 25 of the optic.

The glare-reducing sections 35 and 37 cooperate with the optic 13 to form a circle which may be, for example, 6 millimeters in diameter. The optic 13 forms a central segment of this circle, and the glare-reducing sections 35 and 37 form outer segments of the circle, with the sides 23 and 25 and the edges 41 forming, in effect, chords of the circle. The joining section 39 projects from the periphery of this circle to form a lead-in which facilitates implantation. The width dimension of the optic, i.e., the distance between the sides 23 and 25, may be, for example, about 3 millimeters. The glare-reducing sections 35 and 37 can be moved toward each other over the posterior face 31 against the resilient biasing action of the web 47 to reduce the overall width dimension of the intraocular lens 11 to 3 millimeters or slightly larger than 3 millimeters.

Figure 2:
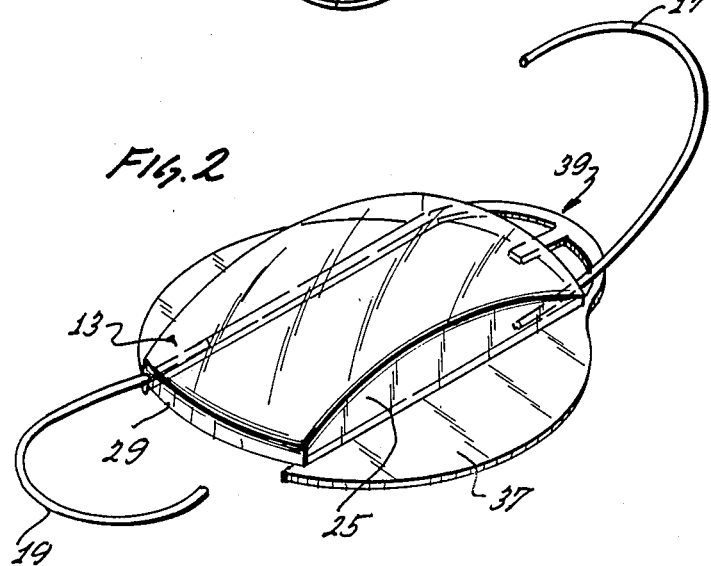
FIG. 2 is an isometric view of the intraocular lens.

Although the fixation means can take various different forms, in the embodiment illustrated, the fixation means includes loops 17 and 19 of polypropylene or other suitable material. Each of the loops 17 and 19 has a proximal end portion 51 which is received within a bore in one of the ends 27 and 29. Alternatively, the loops may be appropriately coupled to the glare attachment 15. Although the loops 17 and 19 may taken different forms, in the illustrated embodiment, each of them is in the form of a resilient "J" loop which is vaulted anteriorly as best shown in FIGS. 2 and 3.

Figure 6:
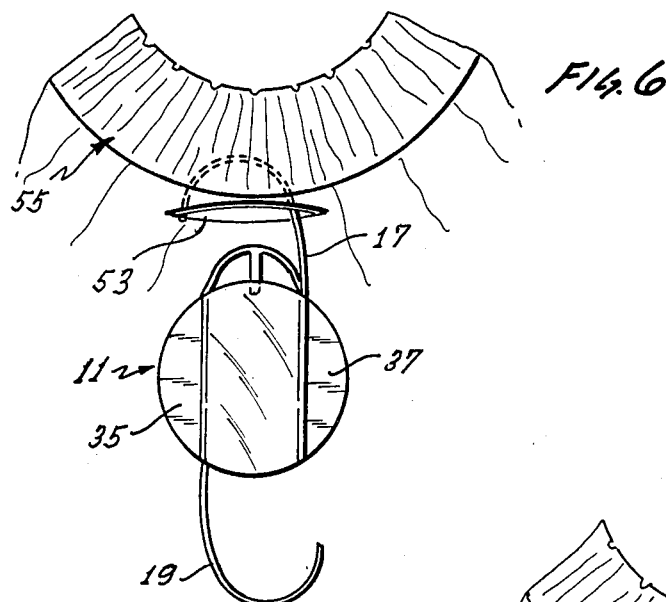
FIGS. 6–8 illustrate how the intraocular lens can be inserted through an incision into the eye.
Figure 7:
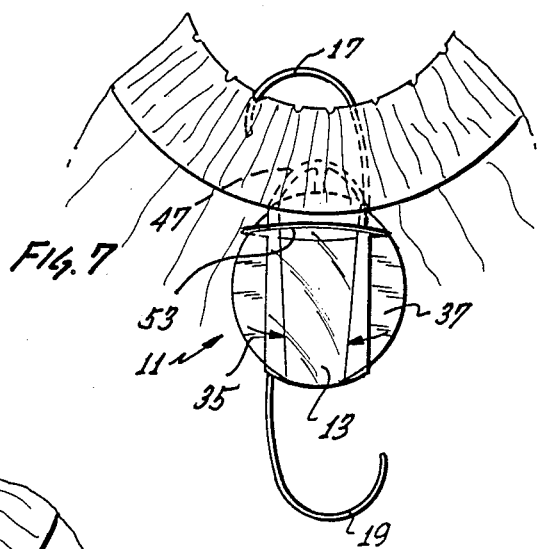
Figure 8:
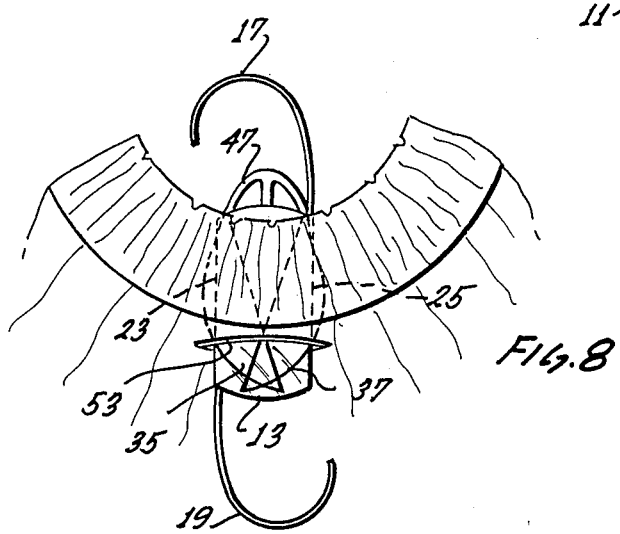

FIGS. 6–8 show one way in which the intraocular lens 11 can be inserted through a relatively small incision 53 into the eye 55 after removal of the natural lens (not shown) through the incision utilizing phacoemulsification. For example, the incision 53 may be of the order of 3.5 to 4 millimeters in length.

FIG. 6 shows the intraocular lens with the loop 17 being inserted through the incision 53 and with the glare-reducing sections 35 and 37 unfolded.

FIG. 7 shows the intraocular lens 11 advanced further through the incision 53 and with the glare-reducing sections 35 and 37 being moved inwardly toward each other along the posterior face 31 of the optic 13 as a result of the resilient deformation of the web 47. FIG. 7 also shows how the joining section 39 forms a lead-in through the incision 53 and across the interior of the eye to facilitate implantation.

FIG. 8 shows the glare-reducing sections moved toward each other sufficiently such that the end portions thereof overlap slightly. In this position, the glare-reducing sections 35 and 37 project only slightly beyond the sides 23 and 25 of the optic 13. The glare-reducing sections 35 and 37 may be cammed to this position by the ends of the incision or held in this position by the surgeon. Accordingly, the intraocular lens 11 can be inserted through the incision 53, even though the incision is only slightly longer than the width of the optic 13.

Figure 9:
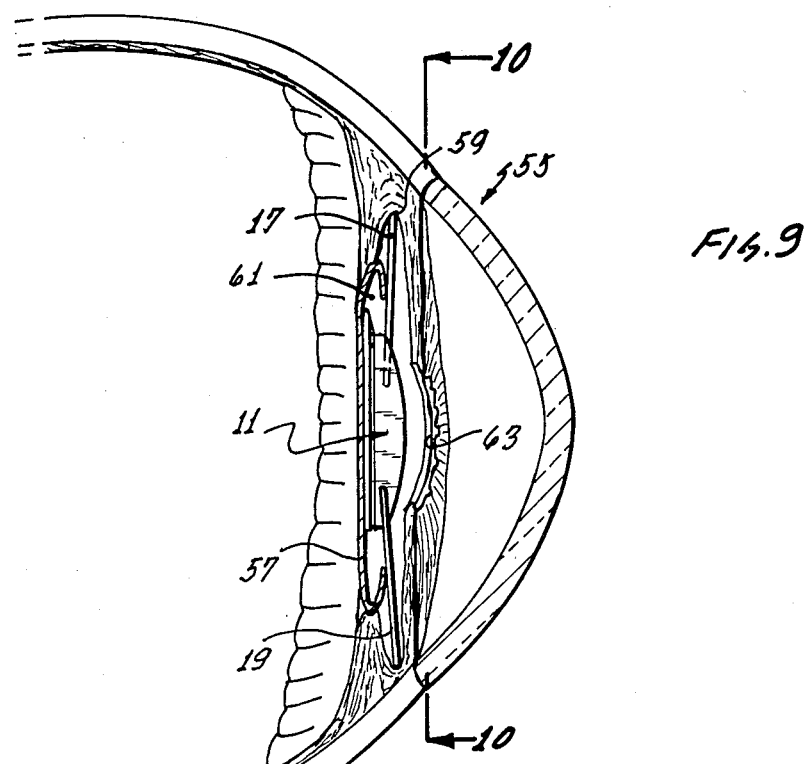
FIG. 9 is a sectional view showing the intraocular lens implanted in the eye.
Figure 10:
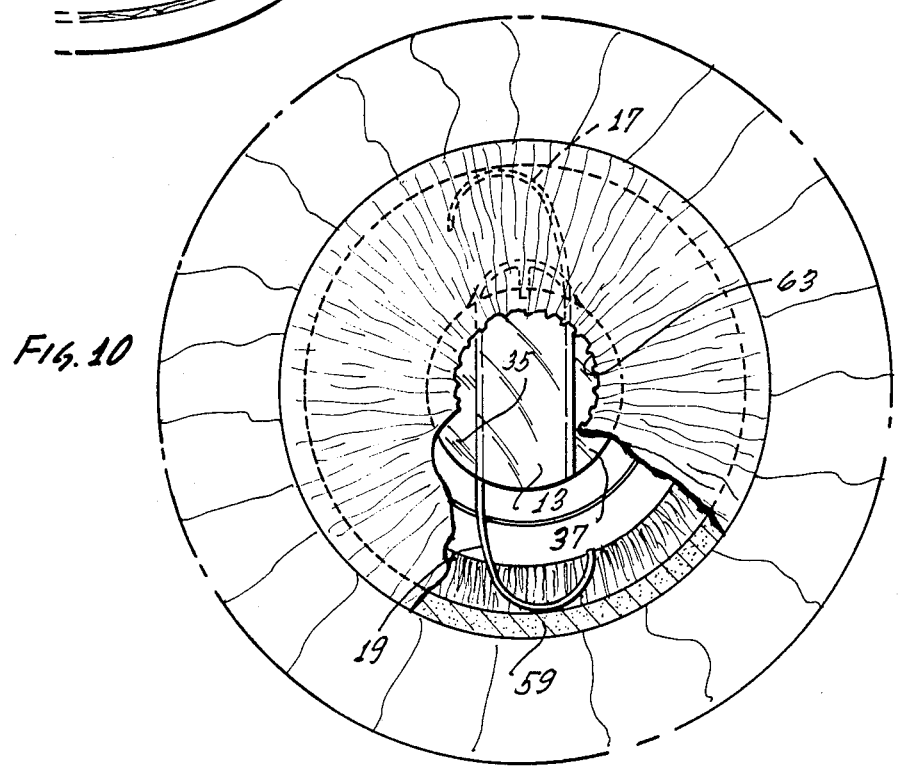
FIG. 10 is a sectional view taken generally along line 10—10 of FIG. 9.

FIGS. 9 and 10 show the intraocular lens 11 implanted in the eye 55. Although the intraocular lens 11 could be implanted within the capsular bag 57, in the embodiment illustrated, the loops 17 and 19 are vaulted anteriorly to engage the ciliary sulcus 59. When so mounted, the intraocular lens 11 is in the posterior chamber 61 coaxial with the pupil 63.

As shown in FIGS. 10, the intraocular lens 11 is implanted so that the optic 13 has its long axis vertical. When implanted, the resilience of the web 47 returns the glare-reducing sections 35 and 37 to the position shown in FIGS. 1-4.

The optic 13 is at the active optical region of the eye 55, and it focuses light passing through it from the pupil 63 on the retina. Because the optic 13 is narrower than the diameter of the active optical region and has an area less than the area of the active optical region, the light outside the optic cannot be focused on the retina. Accordingly, but for the presence of the glare-reducing sections 35 and 37, this light would pass unfocused to the retina and produce glare. However, the glare-reducing sections 35 and 37 substantially reduce transmission of this light to substantially reduce the glare.

Although an exemplary embodiment of the invention has been shown and described, many changes, modifications and substitutions may be made by one having ordinary skill in the art without necessarily departing from the spirit and scope of this invention.

I claim:

1. An intraocular lens implantable in an eye comprising:
    an optic having an optical axis and being elongated in a direction generally transverse to the optical axis whereby the optic has elongated sides;
    glare-reducing means coupled to said optic for reducing glare resulting from light in a zone which extends along at least one of the elongated sides of the optic when the intraocular lens is implanted;
    said glare-reducing means being deformable to permit a reduction in an overall dimension of the intraocular lens for implantation;
    fixation means for fixing the intraocular lens in the eye;
    said glare-reducing means including a first glare-reducing section extending along said one elongated side of the optic and a joining section which joins said first glare-reducing section to the optic, said optic having opposite ends and said joining section projecting beyond one of said ends to form a lead in to facilitate implantation; and
    said joining section including a tab coupled to said optic and extending outwardly beyond said one end of the optic and a web coupled to said tab at a location spaced outwardly of said one end of the optic.

2. An intraocular lens as defined in claim 1 wherein said glare-reducing means transmits a lower percent of incident visible light than the optic.

3. An intraocular lens as defined in claim 1 wherein said glare-reducing means reduces glare resulting from light in first and second zones which are outside the optic and which extend along both of said elongated sides.

4. An intraocular lens as defined in claim 1 wherein said optic is generally in the form of a segment of a circle and said glare-reducing means fills the remainder of the circle.

5. An intraocular lens as defined in claim 1 wherein said optic is rigid.

6. An intraocular lens as defined in claim 1 wherein the web is generally concave toward said one end of said optic, said glare-reducing means includes a second glare-reducing section extending along the other of said elongated sides of the optic, said second glare-reducing section being joined to the web and said web is resilient.

7. An intraocular lens implantable in an eye comprising:
    an optic having an optical axis and being elongated in a direction generally transverse to the optical axis whereby the optic has elongated sides;
    glare-reducing means coupled to said optic for reducing glare resulting from light in a zone which extends along at least one of the elongated sides of the optic when the intraocular lens is implanted;
    said glare-reducing means being deformable to permit a reduction in an overall dimension of the intraocular lens for implantation;
    fixation means for fixing the intraocular lens in the eye;
    said glare-reducing means including a first glare-reducing section extending along said one elongated side of the optic and a joining section which joins said first glare-reducing section to the optic, said optic having opposite ends and said joining section projecting beyond one of said ends to form a lead in to facilitate implantation; and
    said joining section including a tab coupled to the optic and a resiliently deformable web coupling the glare-reducing section to the tab.

8. An intraocular lens as defined in claim 7 wherein the glare-reducing means transmits no more than about 10 percent of visible light incident thereon.

9. An intraocular lens as defined in claim 7 wherein said optic has a posterior face and said glare-reducing section overlaps the posterior face of the optic along said one elongated side.

10. An intraocular lens as defined in claim 7 wherein said glare-reducing section is flexibly joined to the optic by the joining section so that the glare-reducing section can be deflected over the optic for implantation.

11. An intraocular lens as defined in claim 7 wherein said glare-reducing means includes a second glare-reducing section extending along the other of said elongated sides of the optic, said second glare-reducing section being joined to the joining section.

12. An intraocular lens as defined in claim 11 wherein said optic is rigid, each of said glare-reducing sections transmits no more than about 10 percent of the visible incident light thereon, said optic has opposite ends, and said optic has a posterior face and said first and second glare-reducing sections lie generally posteriorly of said posterior face.

* * * * *